(12) United States Patent
McDowall et al.

(10) Patent No.: US 12,102,488 B2
(45) Date of Patent: Oct. 1, 2024

(54) DISPLAY WITH FOLDED OPTICAL PATH

(71) Applicant: Intuitive Surgical Operations, Inc., Sunnyvale, CA (US)

(72) Inventors: Ian E. McDowall, Woodside, CA (US); Randal P. Goldberg, San Mateo, CA (US); Yu-min Lee, Saratoga, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1097 days.

(21) Appl. No.: 16/965,755

(22) PCT Filed: Jan. 30, 2019

(86) PCT No.: PCT/US2019/015903
§ 371 (c)(1),
(2) Date: Jul. 29, 2020

(87) PCT Pub. No.: WO2019/152552
PCT Pub. Date: Aug. 8, 2019

(65) Prior Publication Data
US 2021/0030509 A1 Feb. 4, 2021

Related U.S. Application Data

(60) Provisional application No. 62/624,653, filed on Jan. 31, 2018.

(51) Int. Cl.
*A61B 90/00* (2016.01)
*A61B 34/35* (2016.01)
*G02B 27/01* (2006.01)

(52) U.S. Cl.
CPC .............. *A61B 90/37* (2016.02); *A61B 34/35* (2016.02); *A61B 90/361* (2016.02);
(Continued)

(58) Field of Classification Search
CPC ....... A61B 90/37; A61B 34/35; A61B 90/361; A61B 2090/372; A61B 34/37; A61B 2090/364; G02B 27/0172; G02B 27/0176
See application file for complete search history.

(56) References Cited

U.S. PATENT DOCUMENTS 5,303,085 A 4/1994 Rallison
8,488,246 B2 7/2013 Border et al.
(Continued)

FOREIGN PATENT DOCUMENTS

CN 103149737 A 6/2013
CN 103620479 A 3/2014
(Continued)

OTHER PUBLICATIONS

International Search Report and Written Opinion for Application No. PCT/US2019/015903, mailed on May 17, 2019, 8 pages.
(Continued)

*Primary Examiner* — Alexei Bykhovski (57) ABSTRACT

The technology described in this document can be embodied in a viewing apparatus for a surgical device, the apparatus including a lens assembly including a first polarizer, a display device configured to present an image of a surgical scene, and a reflective surface oriented at an acute angle with respect to the display device such that light from the display device is reflected from the reflective surface towards the lens assembly. The first polarizer in the lens assembly is configured such that light reflected from the reflective surface passes through the first polarizer, and light reaching the first polarizer without being reflected from the reflective surface is substantially blocked.

20 Claims, 6 Drawing Sheets

(52) U.S. Cl.
CPC ..... *G02B 27/0172* (2013.01); *G02B 27/0176* (2013.01); *A61B 2090/372* (2016.02)

(56) References Cited

U.S. PATENT DOCUMENTS

| | | | |
|---|---|---|---|
| 2002/0167645 A1* | 11/2002 | Johnson | B41J 2/435 |
| | | | 353/20 |
| 2015/0205035 A1 | 7/2015 | Border et al. | |
| 2015/0248014 A1* | 9/2015 | Powell | G02F 1/1334 |
| | | | 359/479 |
| 2016/0278695 A1 | 9/2016 | Wang et al. | |
| 2017/0143442 A1* | 5/2017 | Tesar | H04N 23/63 |
| 2017/0176745 A1* | 6/2017 | Poon | G02B 27/286 |
| 2017/0336609 A1 | 11/2017 | Lerner et al. | |
| 2018/0172999 A1 | 6/2018 | Sulai et al. | |

FOREIGN PATENT DOCUMENTS

| | | | |
|---|---|---|---|
| CN | 107111143 | * | 8/2017 |
| WO | WO-2013025530 A1 | | 2/2013 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

DISPLAY WITH FOLDED OPTICAL PATH

CROSS-REFERENCE TO RELATED APPLICATIONS

This application is a U.S. National Stage Application under 35 U.S.C. § 371 and claims the benefit of International Patent Application No. PCT/US2019/015903 titled "Display with Folded Optical Path," filed on Jan. 30, 2019, which claims the benefit of U.S. Provisional Application No. 62/624,653 titled "Display with Folded Optical Path," filed on Jan. 31, 2018. The entire contents of the foregoing applications are hereby incorporated by reference.

TECHNICAL FIELD

This disclosure relates to display devices that may be used in robotic surgical systems.

BACKGROUND

Minimally invasive telesurgical systems for use in surgery are being developed to increase a surgeon's dexterity as well as to allow a surgeon to operate on a patient from a remote location. Telesurgery is a general term for surgical systems where the surgeon uses some form of remote control, e.g., a servomechanism, or the like, to manipulate surgical instrument movements rather than directly holding and moving the instruments by hand. In such a telesurgery system, the surgeon is provided with an image of the surgical site through a display device. Based on visual feedback received through the display device, the surgeon performs the surgical procedures on the patient by manipulating master control input devices, which in turn control the motion of telerobotic instruments.

SUMMARY

In one aspect, this document describes a viewing apparatus for a surgical device, the apparatus including a lens assembly including a first polarizer, a display device configured to present an image of a surgical scene, and a reflective surface oriented at an acute angle with respect to the display device such that light from the display device is reflected from the reflective surface towards the lens assembly. The first polarizer in the lens assembly is configured such that light reflected from the reflective surface passes through the first polarizer, and light reaching the first polarizer without being reflected from the reflective surface is substantially blocked.

In another aspect, this document describes a stereoscopic display apparatus that includes a first display assembly for presenting a first image of a set of two stereo images associated with a surgical scene, and a second display assembly for presenting a second image of the set of two stereo images. The first display assembly includes a first lens assembly, a first display device configured to present the first image, and a first mirror oriented at an acute angle with respect to the first display device such that light from the first display device is reflected from the first mirror towards the first lens assembly. The first lens assembly includes a first polarizer configured such that light reflected from the first mirror passes through the first lens assembly, and light reaching the first polarizer without being reflected from the first mirror is substantially blocked. The second display assembly includes a second lens assembly, a second display device configured to present the second image, and a second mirror oriented at an acute angle with respect to the second display device such that light from the second display device is reflected from the second mirror towards the second lens assembly. The second lens assembly includes a second polarizer configured such that light reflected from the second mirror passes through the second lens assembly, and light reaching the second polarizer without being reflected from the second mirror is substantially blocked.

In another aspect, this document features a surgical system that includes a viewing apparatus, one or more processing devices, and one or more input devices. The viewing apparatus includes a lens assembly including a first polarizer, a display device configured to present an image of a surgical scene, and a reflective surface oriented at an acute angle with respect to the display device such that light from the display device is reflected from the reflective surface towards the lens assembly. The first polarizer in the lens assembly is configured such that light reflected from the reflective surface passes through the first polarizer, and light reaching the first polarizer without being reflected from the reflective surface is substantially blocked. The one or more processing devices are configured to operate the surgical system to perform a surgical process at the surgical scene, and cause presentation of the image of the surgical scene on the display device of the viewing apparatus. The one or more input devices are configured to receive user-input associated with the surgical process in response to presentation of the surgical scene on the display device of the viewing apparatus.

In another aspect, this document features a viewing apparatus for a surgical device, the apparatus including a lens assembly including a first circular polarizer, a display device configured to present an image of a surgical scene, a reflective surface oriented at an acute angle with respect to the display device such that light from the display device is reflected from the reflective surface towards the lens assembly, and a second circular polarizer configured to impart a circular polarization to the light from the display device. The first circular polarizer in the lens assembly is configured such that light reflected from the reflective surface passes through the first circular polarizer, and light reaching the first circular polarizer without being reflected from the reflective surface is substantially blocked. A polarization state of the first circular polarizer can be substantially orthogonal to the polarization state of the second circular polarizer.

Implementations of the above aspects can include one or more of the following features. The light from the display device can be linearly polarized, and the first polarizer can be a linear polarizer having a polarization state that substantially blocks the light reaching the first polarizer without being reflected from the reflective surface. The reflective surface can be a mirror. The polarization state can be diagonal at substantially 45 degrees. The apparatus can include a third polarizer configured to impart a circular polarization to the light from the first display device. The third polarizer can be a quarter wave plate. The polarization state of the first polarizer can be substantially identical to a polarization state of the second polarizer. The first display device can be oriented at an acute angle with respect to the second display device. The first display device can be oriented substantially parallel to the second display device. The first display assembly and the second display assembly can be disposed in a viewing station of a robotic surgical device. The first display assembly and the second display assembly can be disposed in a head-mounted device.

The surgical system can include a robotically controllable surgical instrument, and the one or more processing devices can be configured to control the surgical instrument based on the user-input. The viewing apparatus can include a second polarizer configured to impart a circular polarization to the light from the display device. The first polarizer can be a circular polarizer having a polarization state substantially opposite to a polarization state of the second polarizer.

Some or all of the embodiments described herein may provide one or more of the following advantages. Using one or more polarizers in a folded optical path between a display and the viewer, the technology described herein may allow for the implementation of a device that has a large field of view without visual distractions such as a double images. In some cases, this may increase user-comfort and/or clarity of the presented images (as compared to, for example, devices not using polarizers as described herein). In the particular context of display devices associated with tele-operated surgical systems, this may improve the quality of images presented to a surgeon, and allow the surgeon to comfortably use the display devices while performing a surgical procedure.

DETAILED DESCRIPTION

This document describes a display device in which the observable image, as presented on a screen, is reflected off a mirror, and any direct line of sight to the display is substantially obscured using polarization techniques. The technique described herein can be used in stereoscopic peer-in display device used in an image-guided surgical process such as minimally invasive robot-assisted surgery (also referred to herein as minimally invasive surgery (MIS)). In such display devices, large display screens (e.g., a liquid crystal display (LCD) or a light emitting diode (LED) display) can be used in conjunction with powerful optics to enlarge a field of view for the surgeon. However, in some cases, it may also be important that the images observed by the surgeon is substantially free from visual distractions such as double images to ensure comfortable usability over extended periods of time. The technology described in this document allows for presenting images that are substantially free from visual distractions even when such images are presented using large display screens. For example, one or more polarizers can be used in the optical paths of a display device such that only the rays reflected off a reflective surface (disposed to facilitate a reflected or "folded" optical path) is observable to the viewer, while direct line-of-sight rays are prevented from reaching the viewer's eye via appropriate use of one or more polarizers. This in turn, may allow for reducing visual distractions such as double images that could potentially shift positions or appear/disappear as the surgeon moves his/her eye and/or head. In some cases, the reduction of visual distractions can allow for more comfortable, long-term use of the display device. For example, when used in a stereoscopic display device of a tele-operated surgical system, the technology described herein may allow a surgeon to better visualize a surgical site and/or focus on the surgical process comfortably for an extended period of time without having to experience the visual distractions.

Aspects of the technology are described primarily in terms of an implementation using da Vinci® surgical systems developed by Intuitive Surgical, Inc. of Sunnyvale, California Examples of such surgical systems are the da Vinci® Xi™ Surgical System (Model IS4000) and the da Vinci® Si™ HD™ Surgical System (Model IS3000). It should be understood that aspects disclosed herein may be embodied and implemented in various ways, including computer-assisted, non-computer-assisted, and hybrid combinations of manual and computer-assisted embodiments and implementations. Implementations on da Vinci® Surgical Systems (e.g., surgical simulator, the Model IS4000, the Model IS3000, the Model IS2000, the Model IS1200) are described for illustrative purposes, and are not to be considered as limiting the scope of the inventive aspects disclosed herein. As applicable, inventive aspects may be embodied and implemented in both relatively smaller, handheld, hand-operated devices and relatively larger systems that have additional mechanical support, as well as in other embodiments of computer-assisted tele-operated medical devices. While the technology is described primarily with reference to an example of a peer-in display, the technology may also be used in other types of wearable or non-wearable display devices such as a head-mounted display device used, for example, in virtual or augmented reality (VR/AR) systems.

Figure 1:
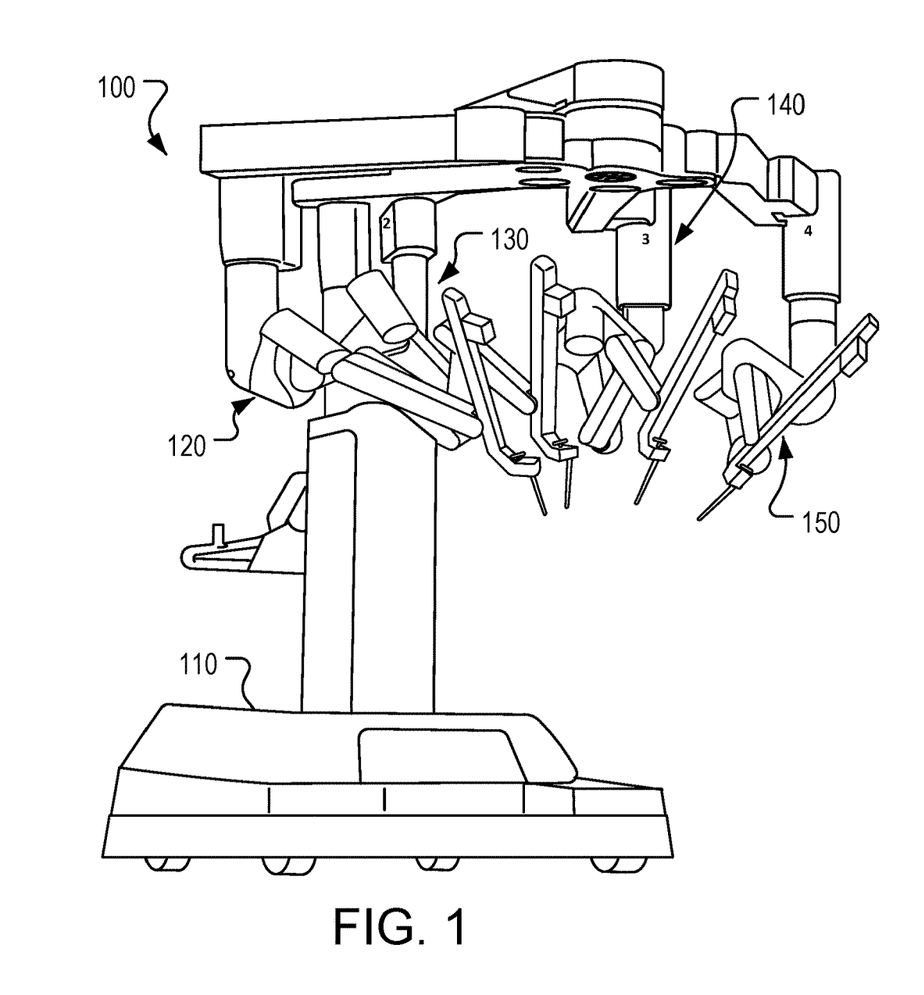
FIG. 1 is a perspective view of an example patient-side cart of a computer-assisted tele-operated surgery system.
Figure 2:
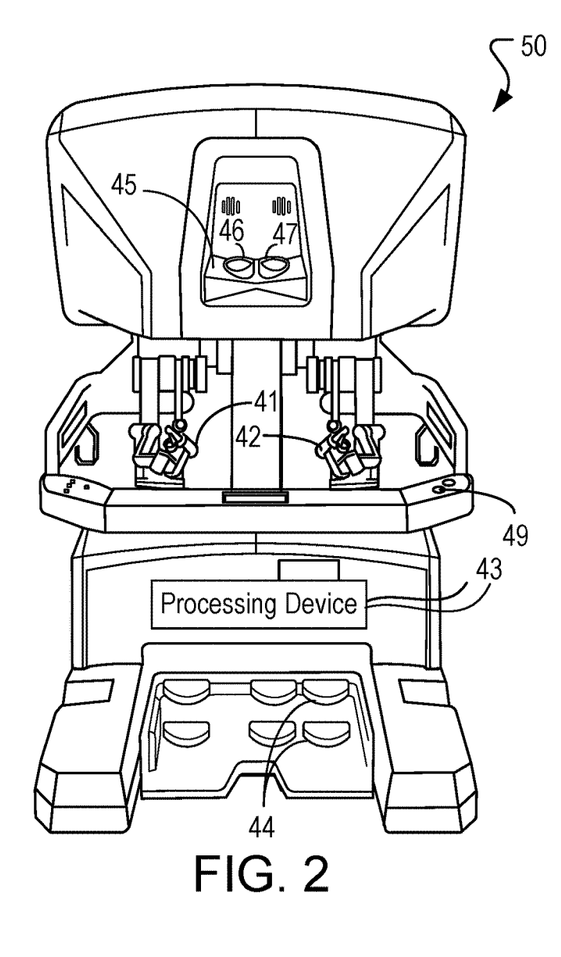
FIG. 2 is a front view of an example surgeon console of a computer-assisted tele-operated surgery system.

Referring to FIGS. 1 and 2, systems for minimally invasive computer-assisted telesurgery (also referred to as MIS) can include a patient-side cart 100 and a surgeon console 50. Telesurgery is a general term for surgical systems where the surgeon uses some form of remote control, e.g., a servo-mechanism, or the like, to manipulate surgical instrument movements rather than directly holding and moving the instruments by hand. The robotically manipulatable surgical instruments can be inserted through small, minimally invasive surgical apertures to treat tissues at surgical sites within the patient body, avoiding the trauma associated with rather large incisions required for open surgery. These robotic systems can move the working ends of the surgical instruments with sufficient dexterity to perform quite intricate surgical tasks, often by pivoting shafts of the instruments at the minimally invasive aperture, sliding of the shaft axially through the aperture, rotating of the shaft within the aperture, and/or the like.

In the depicted embodiment, the patient-side cart 100 includes a base 110, a first robotic manipulator arm assembly 120, a second robotic manipulator arm assembly 130, a third robotic manipulator arm assembly 140, and a fourth robotic manipulator arm assembly 150. Each robotic manipulator arm assembly 120, 130, 140, and 150 is pivotably coupled to the base 110. In some embodiments, fewer than four or more than four robotic manipulator arm assemblies may be included as part of the patient-side cart 100. While in the depicted embodiment the base 110 includes casters to allow ease of mobility, in some embodiments the patient-side cart 100 is fixedly mounted to a floor, ceiling, operating table, structural framework, or the like.

In a typical application, two of the robotic manipulator arm assemblies 120, 130, 140, or 150 hold surgical instruments and a third holds a stereo endoscope. The remaining robotic manipulator arm assembly is available so that a third instrument may be introduced at the work site. Alternatively, the remaining robotic manipulator arm assembly may be used for introducing a second endoscope or another image capturing device, such as an ultrasound transducer, to the work site.

Each of the robotic manipulator arm assemblies 120, 130, 140, and 150 is conventionally formed of links that are coupled together and manipulated through actuatable joints. Each of the robotic manipulator arm assemblies 120, 130, 140, and 150 includes a setup arm and a device manipulator. The setup arm positions its held device so that a pivot point occurs at its entry aperture into the patient. The device manipulator may then manipulate its held device so that it may be pivoted about the pivot point, inserted into and retracted out of the entry aperture, and rotated about its shaft axis.

In the depicted embodiment, the surgeon console 50 includes a stereoscopic peer-in display 45 so that the user may view the surgical work site in stereo vision from images captured by the stereoscopic camera of the patient-side cart 100. Left and right eyepieces, 46 and 47, are provided in the stereoscopic peer-in display 45 so that the user may view left and right display screens inside the display 45 respectively with the user's left and right eyes. While viewing typically an image of the surgical site on a suitable viewer or display, the surgeon performs the surgical procedures on the patient by manipulating master control input devices, which in turn control the motion of robotic instruments.

The surgeon console 50 also includes left and right input devices 41, 42 that the user may grasp respectively with his/her left and right hands to manipulate devices (e.g., surgical instruments) being held by the robotic manipulator arm assemblies 120, 130, 140, and 150 of the patient-side cart 100 in preferably six or more degrees-of-freedom ("DOF"). Foot pedals 44 with toe and heel controls are provided on the surgeon console 50 so the user may control movement and/or actuation of devices associated with the foot pedals.

A processing device 43 is provided in the surgeon console 50 for control and other purposes. The processing device 43 performs various functions in the medical robotic system. One function performed by processing device 43 is to translate and transfer the mechanical motion of input devices 41, 42 to actuate their corresponding joints in their associated robotic manipulator arm assemblies 120, 130, 140, and 150 so that the surgeon can effectively manipulate devices, such as the surgical instruments. Another function of the processing device 43 is to implement the methods, cross-coupling control logic, and controllers described herein.

The processing device 43 can include one or more processors, digital signal processors (DSPs), field-programmable gate arrays (FPGAs), and/or microcontrollers, and may be implemented as a combination of hardware, software and/or firmware. Also, its functions as described herein may be performed by one unit or divided up among a number of subunits, each of which may be implemented in turn by any combination of hardware, software and firmware. Further, although being shown as part of or being physically adjacent to the surgeon console 50, the processing device 43 may also be distributed as subunits throughout the telesurgery system. One or more of the subunits may be physically remote (e.g., located on a remote server) to the telesurgery system.

Figure 3:
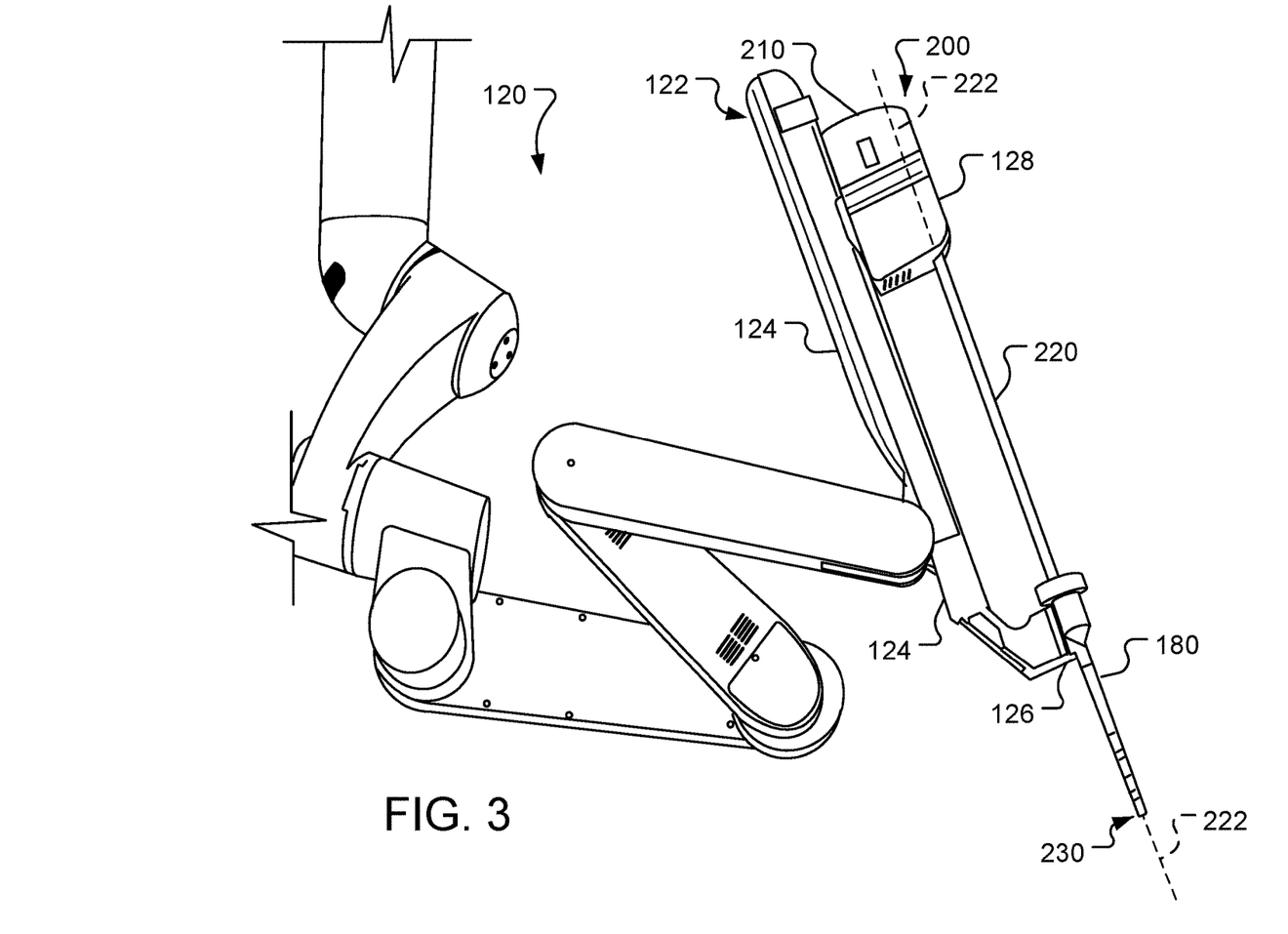
FIG. 3 is a side view of an example robotic manipulator arm assembly of a computer-assisted tele-operated surgery system.

Referring also to FIG. 3, the robotic manipulator arm assemblies 120, 130, 140, and 150 can manipulate devices such as surgical instruments to perform MIS. For example, in the depicted arrangement the robotic manipulator arm assembly 120 is pivotably coupled to an instrument holder 122. A cannula 180 and a surgical instrument 200 are, in turn, releasably coupled to the instrument holder 122. The cannula 180 is a hollow tubular member that is located at the patient interface site during a surgery. The cannula 180 defines a lumen in which an elongate shaft 220 of the surgical instrument 200 is slidably disposed. As described further below, in some embodiments the cannula 180 includes a distal end portion with a body wall retractor member. The instrument holder 122 is pivotably coupled to a distal end of the robotic manipulator arm assembly 120. In some embodiments, the pivotable coupling between the instrument holder 122 and the distal end of robotic manipulator arm assembly 120 is a motorized joint that is actuatable from the surgeon console 50 and processor 43.

The instrument holder 122 includes an instrument holder frame 124, a cannula clamp 126, and an instrument holder carriage 128. In the depicted embodiment, the cannula clamp 126 is fixed to a distal end of the instrument holder frame 124. The cannula clamp 126 can be actuated to couple with, or to uncouple from, the cannula 180. The instrument holder carriage 128 is movably coupled to the instrument holder frame 124. More particularly, the instrument holder carriage 128 is linearly translatable along the instrument holder frame 124. In some embodiments, the movement of the instrument holder carriage 128 along the instrument holder frame 124 is a motorized, translational movement that is actuatable/controllable by the processor 43. The surgical instrument 200 includes a transmission assembly 210, the elongate shaft 220, and an end effector 230. The transmission assembly 210 may be releasably coupled with the instrument holder carriage 128. The shaft 220 extends distally from the transmission assembly 210. The end effector 230 is disposed at a distal end of the shaft 220.

The shaft 220 defines a longitudinal axis 222 that is coincident with a longitudinal axis of the cannula 180. As the instrument holder carriage 128 translates along the instrument holder frame 124, the elongate shaft 220 of the surgical instrument 200 is moved along the longitudinal axis 222. In such a manner, the end effector 230 can be inserted and/or retracted from a surgical workspace within the body of a patient.

The surgical workspace within the body of a patient (the surgical scene) can be presented to the surgeon via the stereoscopic display 45. While the technology described herein primarily uses examples of a peer-in stereoscopic display, other types of stereoscopic and non-stereoscopic displays are also within the scope of the technology. A peer-in stereoscopic display refers to a display that allows a user to look into the display without having to wear it or simultaneously share it with another user. A stereo microscope can be an example of a peer-in stereoscopic display. The stereoscopic display 45, as illustrated in FIG. 2 is another example of a peer-in stereoscopic display.

Figure 4:
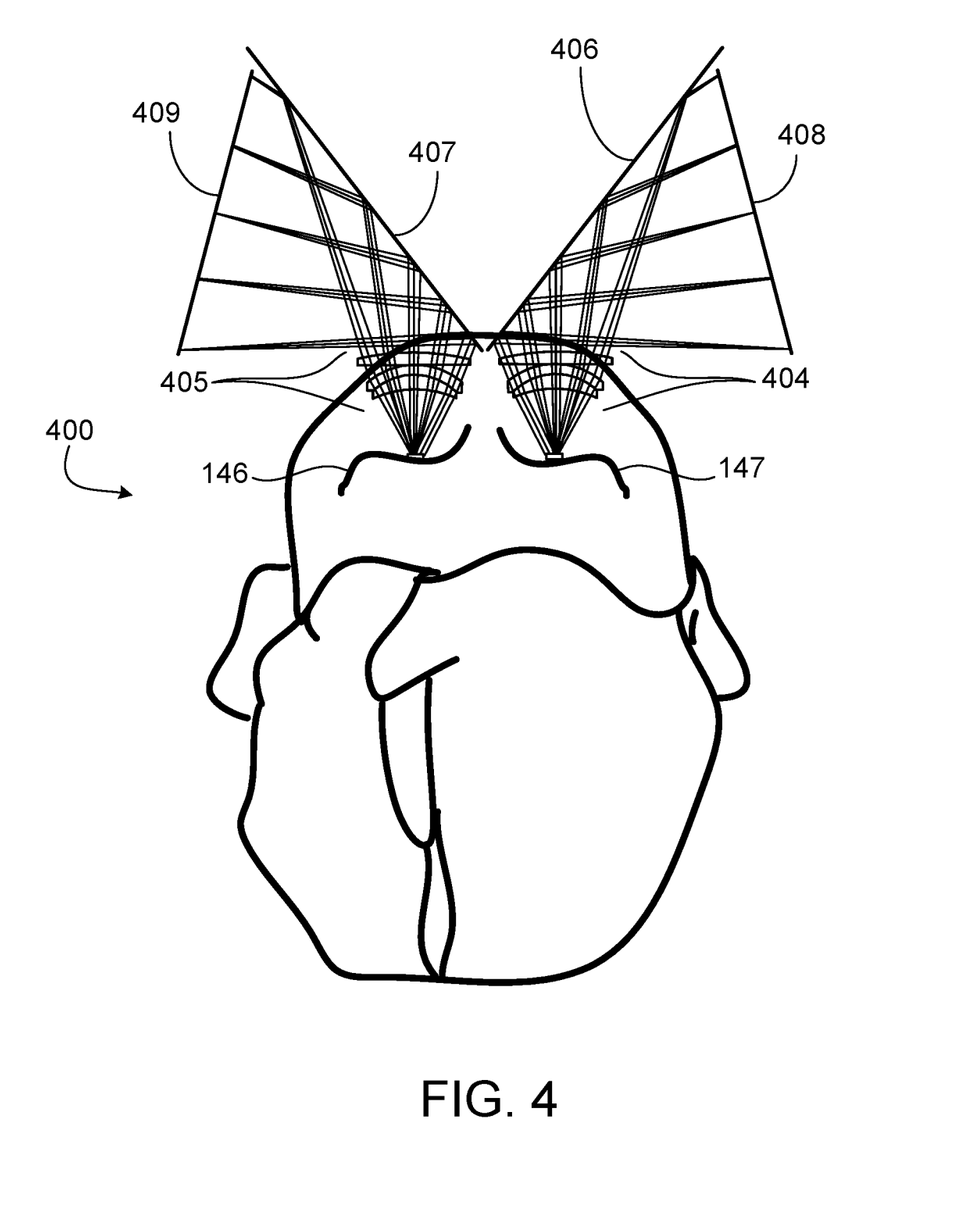
FIG. 4 is a schematic diagram of an example of a display device with folded optical paths.

In some implementations, a peer-in stereoscopic display 45 can include two display screens (one for each eye) and corresponding fold mirrors for reflecting the images presented on the display screens towards the eyepieces 46 and 47. FIG. 4 is a schematic diagram 400 of an example of a display device with folded optical paths. Specifically, FIG. 4 illustrates a user peering in to the eye pieces 46 and 47. In the viewing apparatus for the right eye, light emanates from the display device 408, reflects off the reflective surface 406, and passes through the eyepiece 47 before reaching the user's right eye 147. Similarly, in the viewing apparatus for the left eye, light emanating from display device 409 reflects off the reflective surface 407 and passes through the eyepiece 46 before reaching the user's left eye 146. The relative angles of each set of reflective surface and display device and/or the relative angle between the reflective surfaces can be configured in various ways. For example, the relative angles may be adjusted such that the user perceives the images presented on the display devices as coming from locations that are straight ahead. By allowing for disposing the display devices and the reflective surfaces at angles with one another, a device with folded optical paths (e.g., as illustrated in the schematic diagram 400) facilitates the use of display sizes larger than what would be allowable if the two displays were disposed side by side at locations straight ahead from the user. Also, if placed straight ahead, the two displays could intersect each other.

Figure 5A:
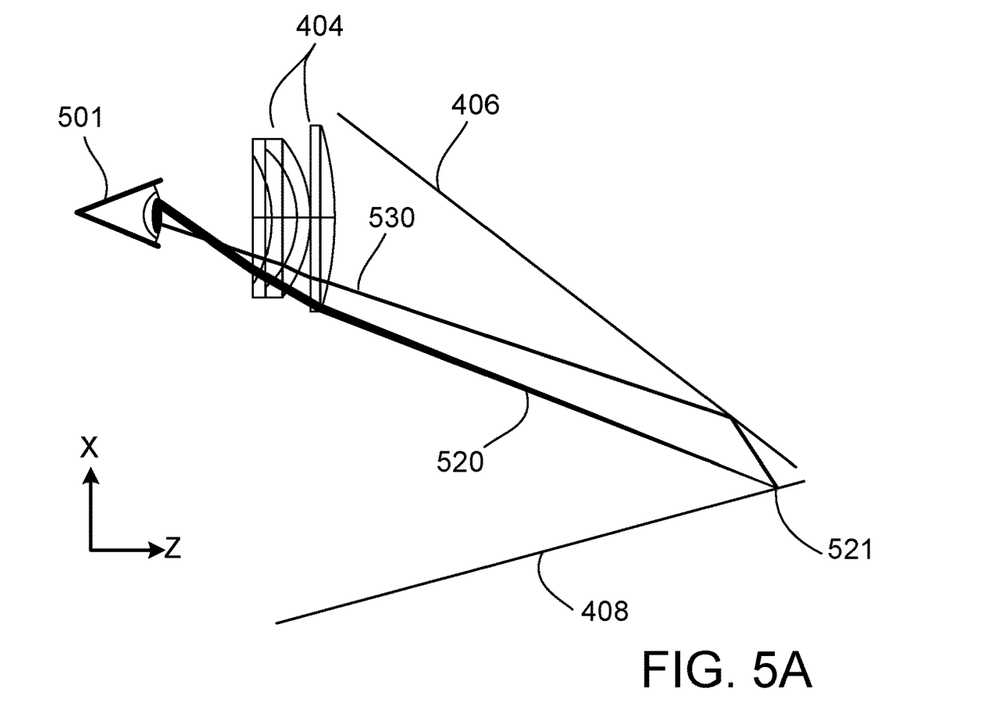
FIGS. 5A and 5B are schematic diagrams illustrating appearance and disappearance, respectively, of a double image due to change in eye positions.
Figure 5B:
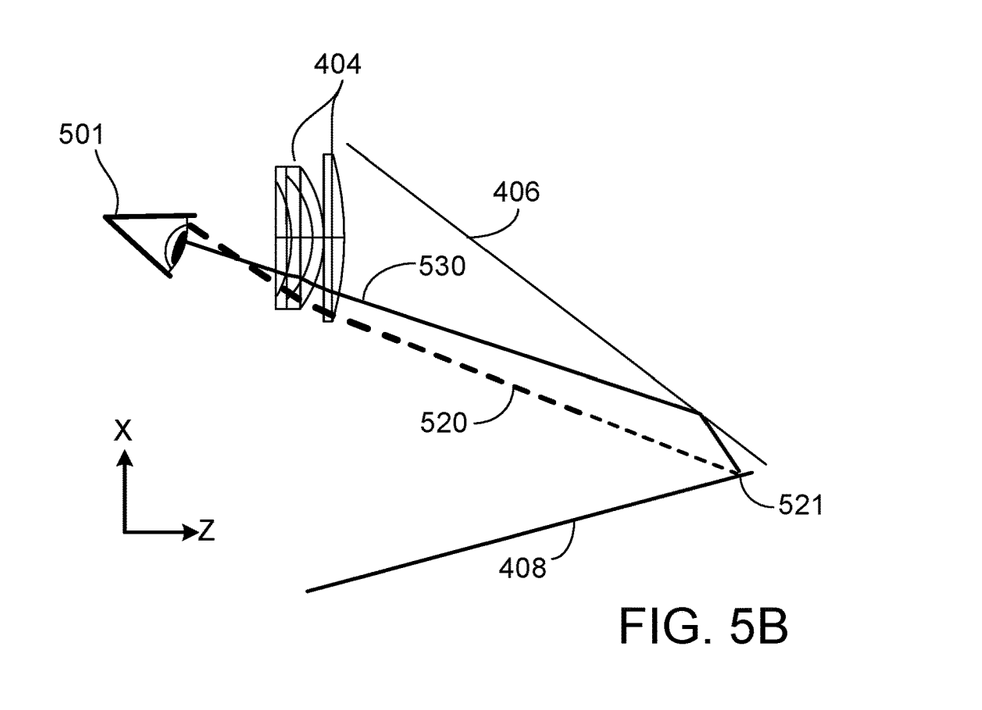

In some implementations, in addition to the size of the display devices, the field of view for the user may also be delimited by the lens assemblies 404 and 405 used in the corresponding viewing apparatus. In some implementations, the field of view for a viewing apparatus may be improved by configuring a lens assembly such that the entire field of view afforded by the corresponding display device is captured by the lens assembly. In some implementations, this may require the display device to be disposed closer to the lens assembly, which in turn may result in a line of sight path between an eyepiece and the corresponding display device. Examples of such configurations are shown in FIGS. 5A and 5B. Specifically, FIG. 5A shows a configuration where light emanating from the point 521 on the display device 408 both via a line of sight path (as illustrated by the ray path 520) as well as the folded optical path facilitated by the reflective surface 406 (as illustrated by the ray path 530). Each of the line of sight path and the folded optical path may be collected by the lens assembly 404 and passed towards the eye 501 of the user. If the position of the eye 501 is as illustrated in FIG. 5A, the light received via the line of sight path 520 as well as the folded optical path 530 enters the eye 501 through the pupil, and as a result, the user perceives two different images corresponding to the same point 521 on the display device 408.

In some cases, the double image perceived by the eye 501 can depend on the location of the eye with respect to the corresponding lens assembly 404. For example, if the position of the eye 501 is changed and oriented as illustrated in FIG. 5B, the line of sight ray path 520 impinges the eye at a location different from that illustrated in FIG. 5A. In some such cases, the line of sight ray path 520 may not intersect with the area of the pupil of the eye 501, and consequently the user may no longer perceive a corresponding image of the point 521 of the display 408. If the head and/or eye position of the user changes again, or the pupil dilates in a way that the line of sight ray path 520 intersects again with the area of the pupil, the second image may again become visible to the user.

The above example illustrates how a user looking at a near-to-eye display may perceive a double image depending on the location of the eye, and how eye rotations, eye motions, pupil dilation, or even subtle changes in pupil location (as can happen, for example, during head motion relative to the display) may cause the double image to appear or disappear. Further, this problem can be pernicious as not all users may be able perceive this, and even when perceived, the artifact may disappear when the tries to look directly at the artifact. Such display issues can significantly detract from the long term comfort and usability of a display apparatus for some users.

In some implementations, the polarization of the light passing through a lens assembly may be controlled in such a way that light traversing the folded optical paths (i.e., reflected off the reflective surface) passes through, but light traversing the line of sight ray path is absorbed by an arrangement of one or more polarizers disposed in the optical path. The polarization states of the light traversing the line of sight ray path is different from the light reflected off the reflective surface. Therefore, one or more polarizers can be appropriately disposed in the optical path of the viewing apparatus such that the one or more polarizers allow the light traversing the line of sight path to pass through while blocking the reflected light.

The polarizers used for selectively blocking the light traversing the line-of-sight path can be of various types. In some implementations, a set of one or more linear polarizers may be used to block the light traversing the line-of-sight path. In some implementations, linearly polarized light emanating from a display device may be first circularly (or elliptically) polarized, and then a set of circular (or elliptical) polarizers may be used to selectively block the circularly polarized light traversing the line-of-sight path. Whether a linear or circular polarization approach is selected for a particular application/apparatus can depend on various factors such as the requirements and performance goals of the system. For example, in some cases, the linear polarization approach may require simpler materials, and/or provide better suppression of the spurious double images as compared to a circular polarization approach. On the other hand, in some cases, a circular polarization approach can potentially better preserve the brightness of the images, and therefore be preferred over a linear approach.

Figure 6:
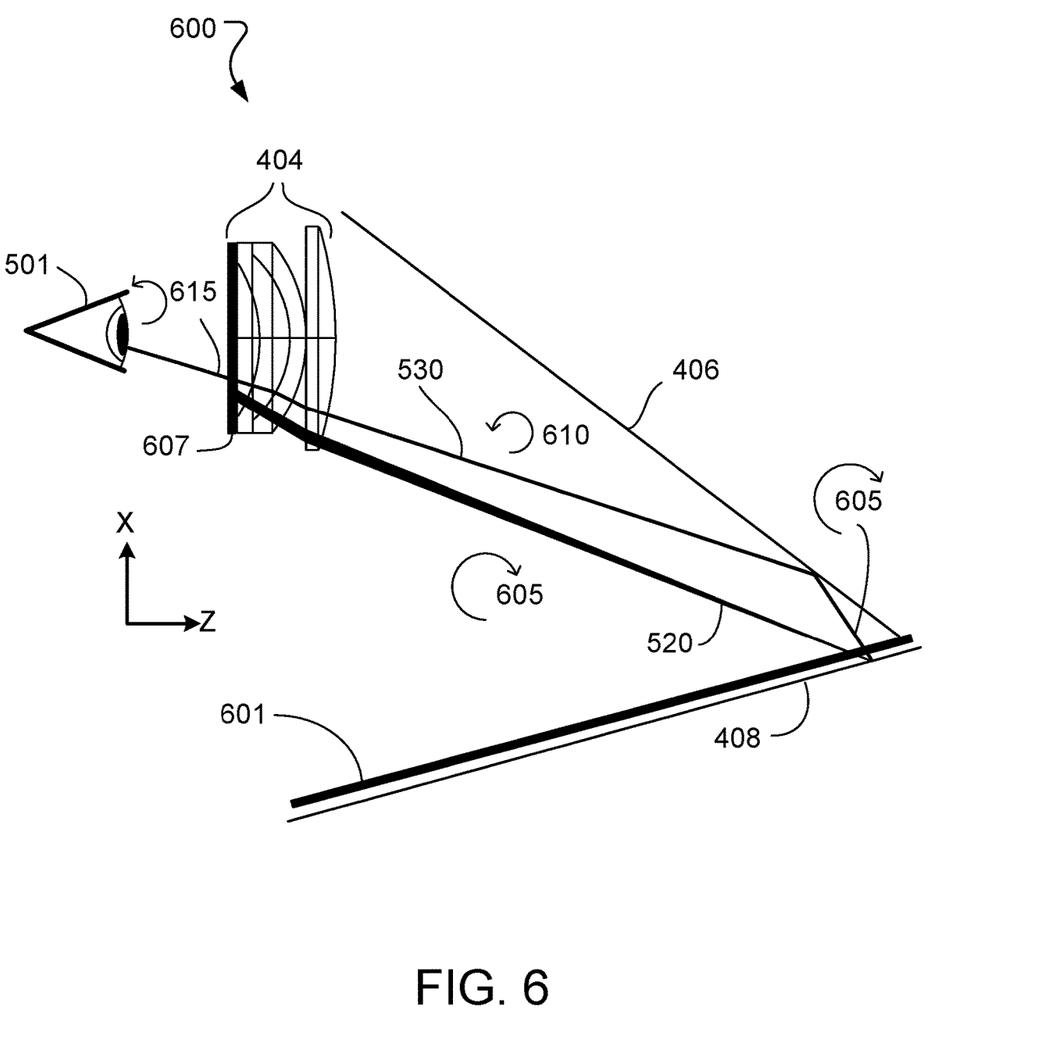
FIG. 6 is a schematic diagram of a device that uses circular polarizers in accordance with technology described herein.

FIG. 6 is a schematic diagram of an example device 600 that uses one or more circular polarizers in accordance with technology described herein. Specifically, in FIG. 6, the display device 408 is a display that radiates linearly polarized light. An LCD is an example of such a display. The device 600 therefore includes an optical element 601 that converts linearly polarized light into circularly polarized light. In some implementations, the device 600 includes a quarter wave plate 601 disposed at an appropriate orientation relative to the linear polarization of the light emanating from the display 408 such that a circular polarization 605 is imparted to the light. The quarter waveplate 601 can include a birefringent material (e.g., polymer, quartz, or mica), for which the index of refraction is different for different orientations of light passing through it. An appropriate waveplate 601 can be selected (e.g., based on the thickness of the material and the variation of the index of refraction for the wavelength of light passing through the waveplate) to introduce a controlled phase shift to the light emanating from the display device 408, thereby altering its polarization. In the example shown in FIG. 6, the direction of circular polarization (also referred to herein as "handedness") 605 of the light emerging from the waveplate 601 is represented using a clockwise arrow. Upon being reflected from the reflective surface 406, the direction or handedness of the light is reversed. In the example of FIG. 6, this circular polarization state 610 is represented using an anticlockwise arrow.

The device 600 also includes a circular polarizer 607 disposed in the optical path of the device 600 to selectively pass light with circular polarization state 610 but block light with circular polarization state 605. In some implementations, the circular polarizer 607 can be disposed between the eye 501 and the lens assembly 404. In some implementations, the circular polarizer 607 can be disposed in the optical path between the lens assembly 404 and the mirror or reflective surface 406. In either case, the light traversing the folded optical path 530 initially emerges from the waveplate 601 with the circular polarization state 605, but has the circular polarization state reversed to the state 610 upon being reflected from the reflective surface 406. This light then passes through the circular polarizer 607 disposed on one side or the other of the lens assembly 404. Because the handedness or direction of the circular polarizer 607 selectively passes light with polarization state 610, the light traversing the folded optical path reaches the eye of the user via the ray path 615. However, the light traversing the line-of-sight ray path from the display device 408 is substantively absorbed or blocked by the circular polarizer 607 because the handedness or polarization state 605 is orthogonal to that of the circular polarizer 607. In some implementations, where the quarter wave plate of the polarizer 607 is disposed in the optical path between the lens assembly 404 and the reflective surface 406, a linear polarizer can be disposed between the eye 501 and the lens assembly 404 to absorb or block unwanted light.

In some implementations, if the display device 408 is inherently unpolarized, an appropriately oriented linear polarizer may be disposed adjacent to the display device 408 to make the light emanating from the display device 408 linearly polarized. For example, if the display device 408 is an organic light emitting diode (OLED) display, a linear polarizer may be disposed between the display device 408 and the quarter wave plate 601. In some implementations, the quarter waveplate 601 and the linear polarizer may be combined in one optical unit to realize a circular polarizer for the display device 408. In some implementations, because the angles of the light emission from the display device 408 may be oblique, the orientation of the quarter waveplate 601 and/or the circular polarizer 607 may have to be adjusted to achieve a target contrast between the perceived image and an unwanted image. This may be balanced against the impact on color fidelity, which may be sometimes degraded by the non-achromatic performance of polarization components.

Figure 7A:
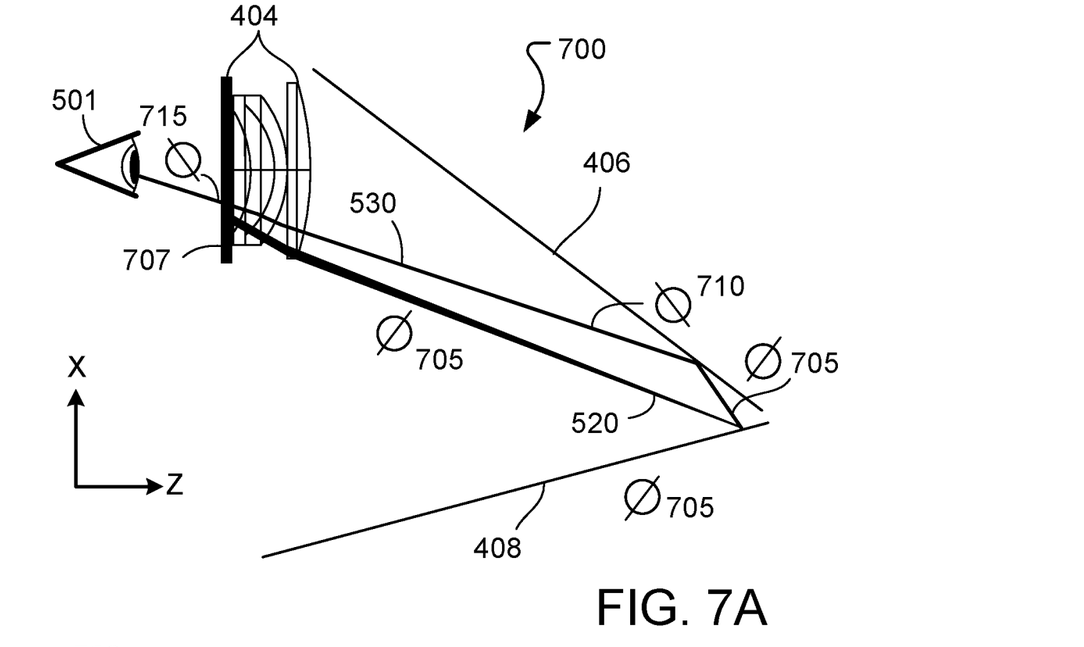
FIGS. 7A and 7B are schematic diagrams of example devices that use linear polarizers in accordance with technology described herein.
Figure 7B:
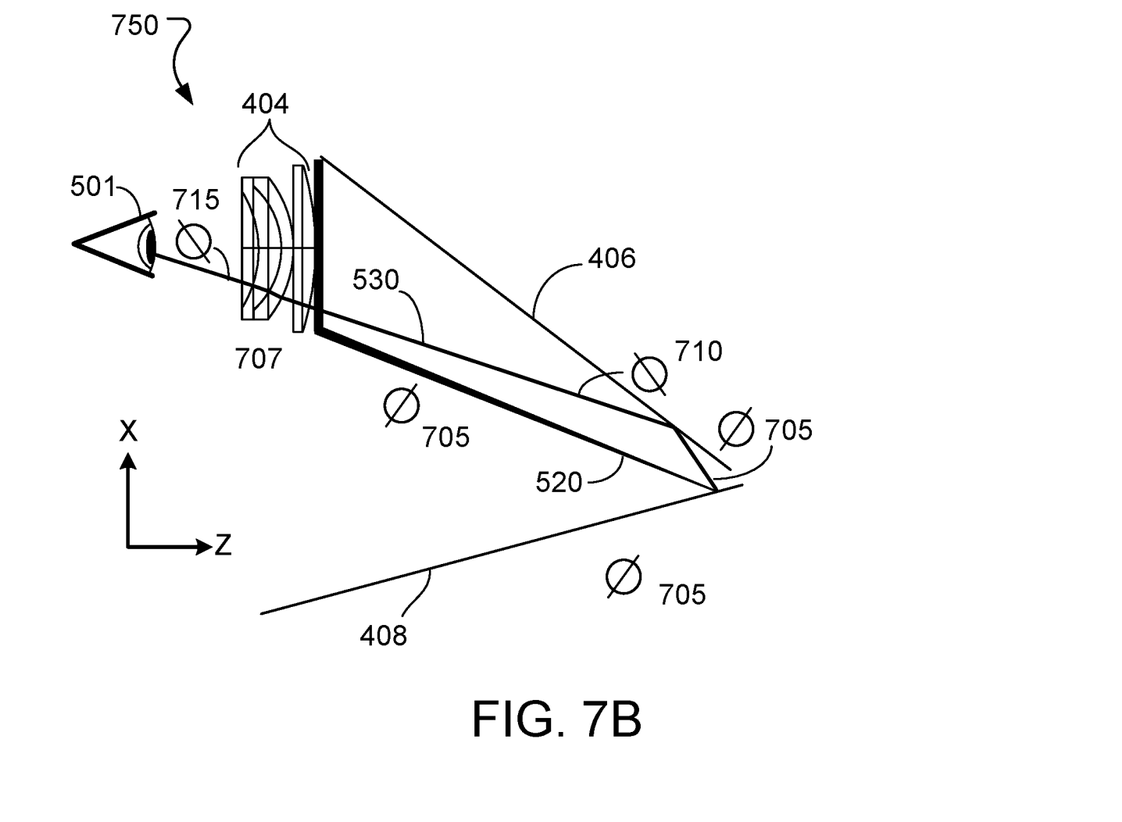

In some implementations, one or more linear polarizers can be used to selectively pass light traversing the folded optical path while blocking light traversing a direct line-of-sight ray path. FIGS. 7A and 7B are schematic diagrams of example devices that use such a linear polarization approach. In these examples, the display devices 408 is an inherently polarized display such as an LCD. In some implementations, the display device 408 may emit light that is linearly polarized diagonally with respect to the horizontal axis of the display. In FIGS. 7A and 7B, such a diagonal polarization state is denoted using the reference numeral 705. In some implementations, if the display device 408 is linearly polarized but not along the diagonal, a waveplate may be disposed adjacent to the display device 408 to impart a diagonal polarization to the emitted light. In some implementations, a supplementary linear polarizer may be added to impart a diagonal polarization to the emitted light. In some such cases, the display device 408 may appear dimmer, but if the display device is adequately bright, the dimming may not be significantly noticeable. In some implementations, an orientation of the display device 408 may be adjusted such that the polarization axis is aligned to an edge of the display to impart the desired diagonal polarization to the emitted light.

In any case, the light emanating from the display device 408 can be configured such that the light is linearly polarized at an angle (e.g., 45 degrees, as represented by the polarization state 705) relative to the horizon. Upon reflection of the light off the reflective surface 406, the polarization state of the light is reversed, and the reflected light in the folded optical path 530 possesses a polarization state 710 (which, as depicted in FIGS. 7A and 7B, is orthogonal to the polarization state 705). In the example device 700 shown in FIG. 7A, a linear polarizer 707 disposed between the eye and the lens assembly 404 is oriented such that the linear polarizer 707 allows passage of the reflected light with polarization state 710 (as depicted by the ray path 715), while preventing the light traversing the line-of-sight ray path 520 from passing through. This can result in the line-of-sight view being substantially occluded from the eye 501, thus enabling it to observe only the image reflected from the reflective surface 406. Occlusion of the line-of-sight view therefore may substantially alleviate the double image artifacts, which in turn may improve long-term usability of the corresponding viewing apparatus.

FIG. 7B shows the example of a device 750 where the linear polarizer 707 is disposed between the lens assembly 404 and the reflective surface 406. In some implementations, this location of the linear polarizer 707 (or a circular polarizer in a device analogous to the one shown in FIG. 6) may provide more eye relief to some users.

The inventive technology has been described above primarily with reference to a single viewing apparatus. However, for a stereoscopic display apparatus, an analogous second viewing apparatus may be provided for the other eye of the user. Specifically, for a computer-assisted tele-operated surgery system (an example of which is depicted in FIG. 1), a stereoscopic viewing apparatus can include a first display assembly and a second display assembly for presenting a first image and a second image, respectively, of a set of two stereo images associated with a surgical scene. Each of the first display assembly and the second display assembly can include a corresponding lens assembly, a display device configured to present the corresponding image, and a reflective surface (e.g., a mirror) oriented at an acute angle with respect to the corresponding display device such that light from the display device is reflected from the first mirror towards the lens assembly. The lens assembly on each side includes a polarizer (e.g., a linear polarizer or a circular polarizer) configured such that light reflected from the reflective surface passes through the lens assembly, and light reaching the polarizer without being reflected from the reflective surface is substantially blocked. In some implementations, the polarization states of light emanating from the lens assemblies may be controlled to enable use of the subject technology for use with polarized glasses. For example, the diagonal polarization techniques described with reference to FIGS. 7A and 7B may be used to control polarization states to enable viewing with polarized glasses such as ones used for 3D viewing in movie theaters.

In some implementations, a computer-assisted tele-operated surgery system including a viewing apparatus as described above can also include one or more processing devices that facilitate the presentation of the stereo images corresponding to the surgical scene on the display devices. The one or more processors may also facilitate operations of the surgery system to perform a surgical process at the surgical scene. For example, the surgery system can include one or more input devices that are configured to receive user-input associated with the surgical process in response to presentation of the surgical scene on the display device of the viewing apparatus. The one or more processing devices can then be configured to control a robotically controllable surgical instrument based on the user-input.

The functionality of the tele-operated surgery system described herein, or portions thereof, and its various modifications (hereinafter "the functions") can be implemented, at least in part, via a computer program product, e.g., a computer program tangibly embodied in an information carrier, such as one or more non-transitory machine-readable media or storage device, for execution by, or to control the operation of, one or more data processing apparatus, e.g., a programmable processor, a DSP, a microcontroller, a computer, multiple computers, and/or programmable logic components.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one or more processing devices at one site or distributed across multiple sites and interconnected by a network.

Actions associated with implementing all or part of the functions can be performed by one or more programmable processors or processing devices executing one or more computer programs to perform the functions of the processes described herein. All or part of the functions can be implemented as, special purpose logic circuitry, e.g., an FPGA and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. Components of a computer include a processor for executing instructions and one or more memory devices for storing instructions and data.

While this specification contains many specific implementation details, these should not be construed as limitations on what may be claimed, but rather as descriptions of features that may be specific to particular embodiments. Other embodiments may also be within the scope of the technology described herein. For example, while the technology has been described with reference to two mirrors and a single mirror bounce, the technology may be extended to any odd number of mirror bounces without deviating from the scope of this disclosure. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Elements of different implementations described herein may be combined to form other embodiments not specifically set forth above. Elements may be left out of the structures described herein without adversely affecting their operation. Furthermore, various separate elements may be combined into one or more individual elements to perform the functions described herein.

What is claimed is:

1. A viewing apparatus for a surgical device, the viewing apparatus comprising:
   a lens assembly including a first polarizer;
   a display device configured to present an image of a surgical scene; and
   a reflective surface oriented at an acute angle with respect to the display device such that light from the display device is reflected from the reflective surface towards the lens assembly,
   wherein the first polarizer in the lens assembly is configured such that light reflected from the reflective surface passes through the first polarizer, and line-of-sight light reaching the first polarizer from the display device without being reflected from the reflective surface is substantially blocked.

2. The viewing apparatus of claim 1, wherein the light from the display device is linearly polarized, and the first polarizer is a linear polarizer having a polarization state that substantially blocks the line-of-sight light reaching the first polarizer without being reflected from the reflective surface.

3. The viewing apparatus of claim 2, wherein the polarization state is diagonal at substantially 45 degrees.

4. The viewing apparatus of claim 1, wherein the reflective surface is a mirror.

5. The viewing apparatus of claim 1, wherein the lens assembly is disposed in a head-mounted device.

6. A stereoscopic display apparatus comprising:
   a first display assembly for presenting a first image of a set of two stereo images associated with a surgical scene, the first display assembly comprising:
   a first lens assembly,
   a first display device configured to present the first image, and
   a first mirror oriented at an acute angle with respect to the first display device such that light from the first display device is reflected from the first mirror towards the first lens assembly,
   wherein the first lens assembly includes a first polarizer configured such that light reflected from the first mirror passes through the first lens assembly, and line-of-sight light reaching the first polarizer from the first display device without being reflected from the first mirror is substantially blocked; and
   a second display assembly for presenting a second image of the set of two stereo images, the second display assembly comprising:
   a second lens assembly,
   a second display device configured to present the second image, and
   a second mirror oriented at an acute angle with respect to the second display device such that light from the second display device is reflected from the second mirror towards the second lens assembly,
   wherein the second lens assembly includes a second polarizer configured such that light reflected from the second mirror passes through the second lens assembly, and line-of-sight light reaching the second polarizer from the second display device without being reflected from the second mirror is substantially blocked.

7. The stereoscopic display apparatus of claim 6, further comprising a third polarizer configured to impart a circular polarization to the light from the first display device.

8. The stereoscopic display apparatus of claim 7, wherein the third polarizer is a quarter wave plate.

9. The stereoscopic display apparatus of claim 6, wherein the light from the first display device is linearly polarized, and the first polarizer is a linear polarizer having a polarization state that substantially blocks the light reaching the first polarizer without being reflected from the first mirror.

10. The stereoscopic display apparatus of claim 6, wherein a polarization state of the first polarizer is substantially identical to a polarization state of the second polarizer.

11. The stereoscopic display apparatus of claim 6, wherein the first display device is oriented at an acute angle with respect to the second display device.

12. The stereoscopic display apparatus of claim 6, wherein the first display device is oriented substantially parallel to the second display device.

13. The stereoscopic display apparatus of claim 6, wherein the first display assembly and the second display assembly are disposed in a viewing station of a robotic surgical device.

14. The stereoscopic display apparatus of claim 6, wherein the first display assembly and the second display assembly are disposed in a head-mounted device.

15. The stereoscopic display apparatus of claim 6, wherein the stereoscopic display apparatus is disposed in a viewing station of a robotic surgical device.

16. A surgical system comprising:
a viewing apparatus comprising:
a lens assembly including a first polarizer,
a display device configured to present an image of a surgical scene, and
a reflective surface oriented at an acute angle with respect to the display device such that light from the display device is reflected from the reflective surface towards the lens assembly,
wherein the first polarizer in the lens assembly is configured such that light reflected from the reflective surface passes through the first polarizer, and line-of-sight light reaching the first polarizer from the display device without being reflected from the reflective surface is substantially blocked;
one or more processing devices configured to:
operate the surgical system to perform a surgical process at the surgical scene, and
cause presentation of the image of the surgical scene on the display device of the viewing apparatus; and
one or more input devices configured to receive user-input associated with the surgical process in response to presentation of the surgical scene on the display device of the viewing apparatus.

17. The surgical system of claim 16, further comprising a robotically controllable surgical instrument, and the one or more processing devices are configured to control the robotically controllable surgical instrument based on the user-input.

18. The surgical system of claim 16, wherein the viewing apparatus further comprises a second polarizer configured to impart a circular polarization to the light from the display device.

19. The surgical system of claim 18, wherein the first polarizer is a circular polarizer having a polarization state substantially opposite to a polarization state of the second polarizer.

20. The surgical system of claim 16, wherein the light from the display device is linearly polarized, and the first polarizer is a linear polarizer having a polarization state that substantially blocks the line-of-sight light reaching the first polarizer without being reflected from the reflective surface.

* * * * *